United States Patent [19]

Bernardi

[11] Patent Number: 5,298,022

[45] Date of Patent: * Mar. 29, 1994

[54] WEARABLE ARTIFICIAL PANCREAS

[75] Inventor: Luigi Bernardi, Milan, Italy

[73] Assignee: Amplifon SpA, Milan, Italy

[ * ] Notice: The portion of the term of this patent subsequent to Jan. 5, 2010 has been disclaimed.

[21] Appl. No.: 238

[22] Filed: Jan. 4, 1993

Related U.S. Application Data

[63] Continuation-in-part of Ser. No. 527,129, May 22, 1990, Pat. No. 5,176,632.

[30] Foreign Application Priority Data

May 29, 1989 [IT] Italy ............................... 48005 A/89

[51] Int. Cl.$^5$ ............................................. A61M 31/00
[52] U.S. Cl. ....................................... 604/66; 128/635
[58] Field of Search .............. 604/45, 27, 28, 50-52, 604/65-67; 128/632, 635

[56] References Cited

U.S. PATENT DOCUMENTS

| | | | |
|---|---|---|---|
| 3,512,517 | 5/1970 | Kadish et al. | 604/27 |
| 4,515,584 | 5/1985 | Abe et al. | 604/66 |
| 4,526,569 | 7/1985 | Bernardi | 604/65 |
| 5,176,632 | 1/1993 | Bernardi | 604/66 |

Primary Examiner—Jerome L. Kruter
Attorney, Agent, or Firm—Bucknam and Archer

[57] ABSTRACT

A device for the continuous quantitative determination of glucose in the blood of a diabetic patient over a period of 24–36 hours, comprises a container for a saline solution with heparin, a microdialyzing needle inserted into a vein of a diabetic patient, a pump for injecting the solution into the microdialyzing needle, a semipermeable hollow fiber membrane located externally of the needle whereby dialysis occurs between the blood and the solution and only glucose and other substances of low molecular weight below 100,000 daltons go through the membrane and the concentration of the glucose and other substances of low molecular weight below 100,000 daltons inside the needle is proportional to that of the external side of the membrane. The needle is provided with an outgoing conduit, the conduit leads to a sensor, which comprises an enzymatic membrane coupled with a Platinum-Silver electrode. The glucose goes into the conduit, oxidation of glucose to gluconic acid and hydrogen peroxide occurs and the hydrogen peroxide is decomposed to give $H_2O$ and oxygen with the liberation of two electrons whereby electric current is produced and the concentration of glucose in the blood is determined by determining the amount of current produced.

It is possible to vary the dilution ratio of the fluid circulating inside the microdialyzing needle by varying the pump speed so that it is possible to have a ratio of the glucose containing saline solution to the actual concentration of glucose in the blood of $\frac{1}{2}$–1/20.

2 Claims, 5 Drawing Sheets

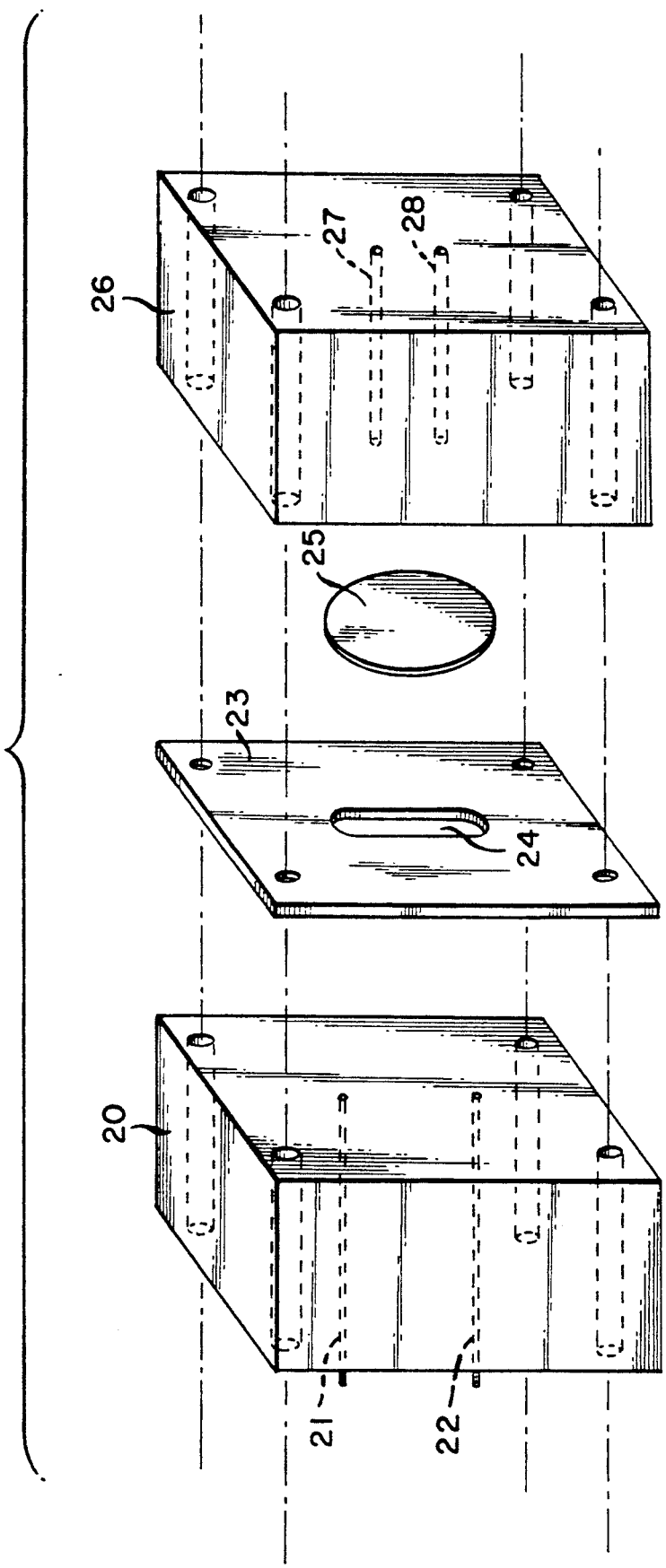

WEARABLE ARTIFICIAL PANCREAS

This application is a continuation-in-part of U.S. Ser. No. 527,129 filed May 22, 1990, now U.S. Pat. No. 5,176,632, the subject matter of which is incorporated herein by reference.

The invention of Ser. No. 527,129, now U.S. Pat. No. 5,176,632, relates to extracorporeal devices to be worn by an individual for the continuous quantitative determination over a period of 24-36 hours of low molecular weight substances below 100,000 daltons, the concentration of which varies continuously in the human body, without removing the blood from the individual. More specifically, the invention of Ser. No. 527,129, U.S. Pat. No. 5,176,632, relates to the continuous quantitative determination of substances such as glucose in the case of diabetic people. It could also be applied to the determination of lactate in athletes or in people with heart diseases, without removing blood from the body, while allowing the individual to carry on his normal activities. Further, the device in the case of diabetic people may act as a wearable artificial extracorporeal endocrine pancreas because it may also provide for the injection of insulin depending upon the measurements obtained.

The crux of the invention in Ser. No. 527,129, now U.S. Pat. No. 5,176,632, resides in carrying out the dialysis in the body by means of a microdialyzing needle which is inserted into a vein of the patient. A semipermeable hollow fiber membrane surrounds the terminal part of the needle. Substances of low molecular weight, particularly glucose, or lactate go through the membrane, while the higher molecular weight substances, such as fibrin, and cells do not go through. Further, a solution containing heparin is introduced into the needle in order to prevent blood clotting in the proximity of its terminal part. The liquid flows into the space between the needle and the hollow fiber membrane. Proportional equilibrium is reached between the solution being introduced through the needle and the blood which flows outside the membrane. The solution then flows to an enzymatic-amperometric sensor used to determine quantitatively the amount of glucose or lactate. One advantage of the invention of Ser. No. 527,129 is that only 1/10 of the glucose in the blood is measured. In other words, the dialysis is not carried out while the actual concentration of glucose in the saline solution is identical to the concentration of glucose in the blood of a diabetic patient but only while it is in proportion to it, that is one tenth of it. The glucose concentration in a diabetic patient could be as much as 7-8 mg/cc. The sensor can only measure up to 0.7-0.8 mg/cc. Most of the known sensors are linear in the range which is 1/10 of the actual glucose concentration in the blood. It was stressed in Ser. No. 527,129 that this feature is new because with other devices it is necessary to wait for the glucose in the solution to be exactly identical to the concentration of glucose in the blood of the patient. However, since the sensor cannot measure more than 0.7-0.8 mg/cc, the known devices may not be operative and the known sensors may not measure the actual glucose concentration.

It has also been shown in Ser. No. 527,129 that an open path is used, that is the saline solution is not recirculated but is discarded and only a small amount of blood is actually used.

It has now been found that the dilution ratio of the fluid circulating in the interior of the microdialyzing needle may be varied by varying the pump speed so that the dilution ratio may be varied over a range of ½ to 1/20.

BRIEF DESCRIPTION OF THE DRAWINGS

The invention is illustrated further by reference to the accompanying drawings which are the same as in Ser. No. 527,129.

FIG. 5 is an exploded view of the measurement cell.

Figure 1:
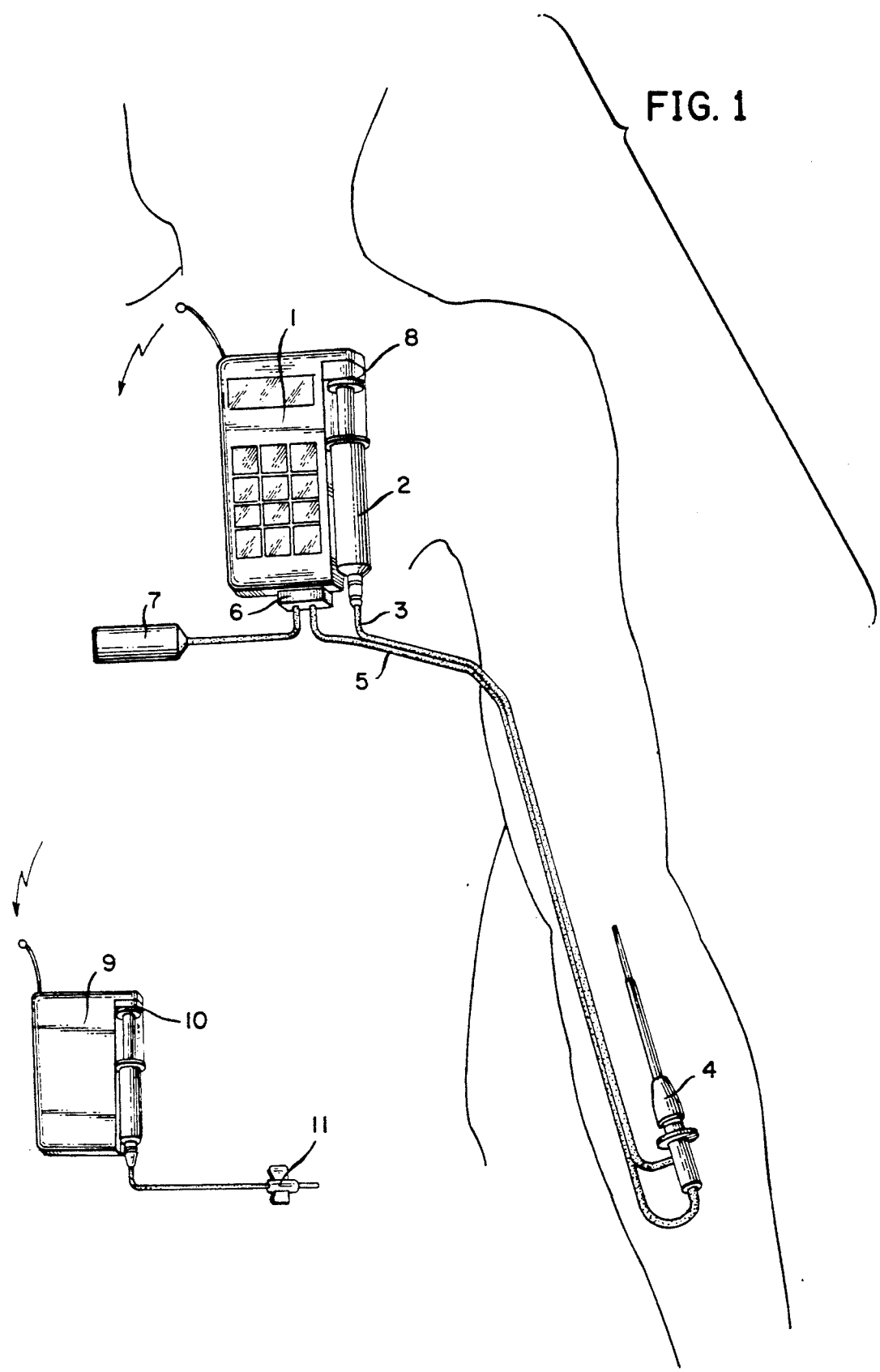
FIG. 1 is the overall apparatus, comprising the monitoring unit and the infusion device.
Figure 2:
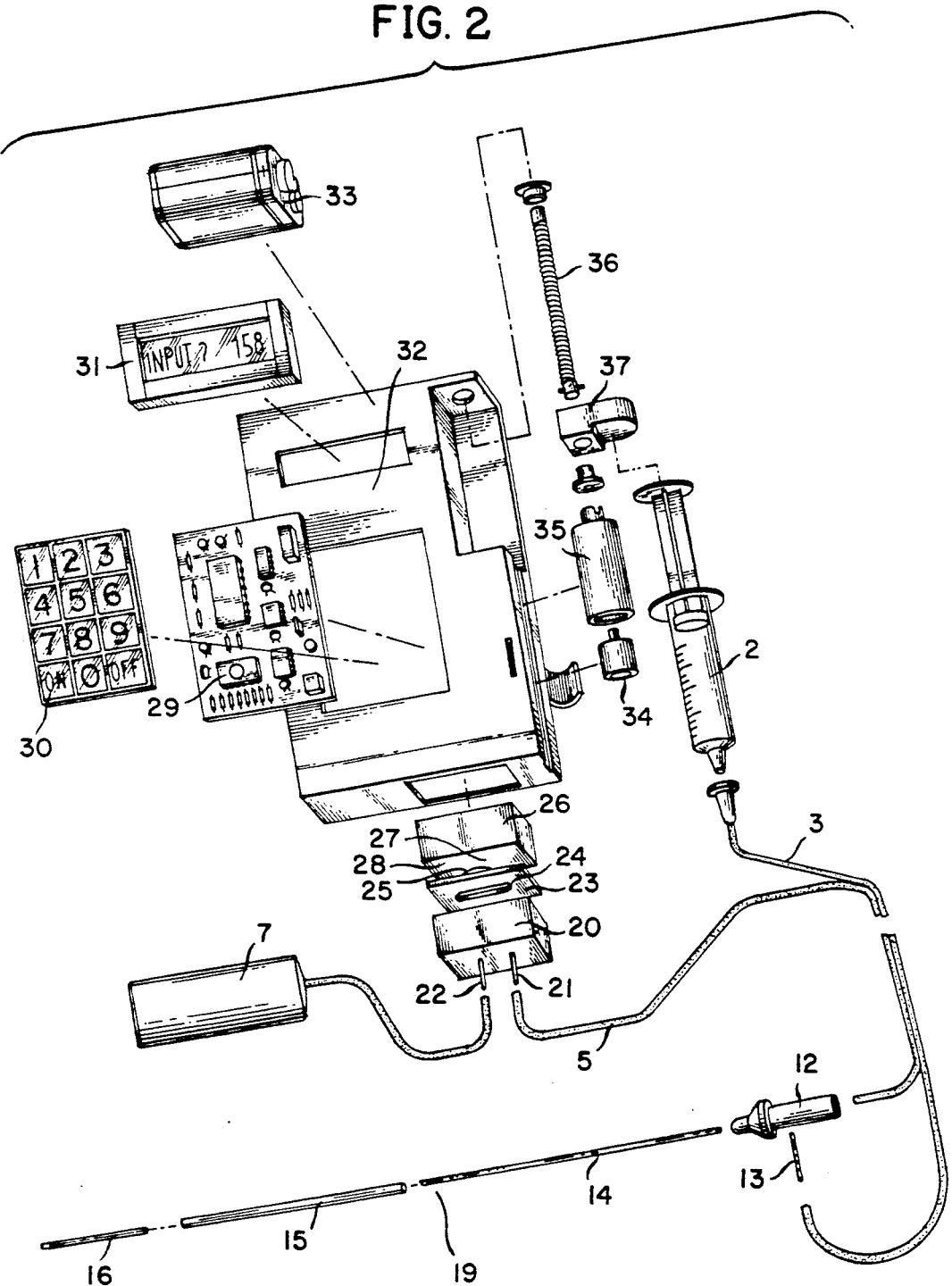
FIG. 2 is an exploded view of the apparatus used for measuring the glucose in the human body.
Figure 3:
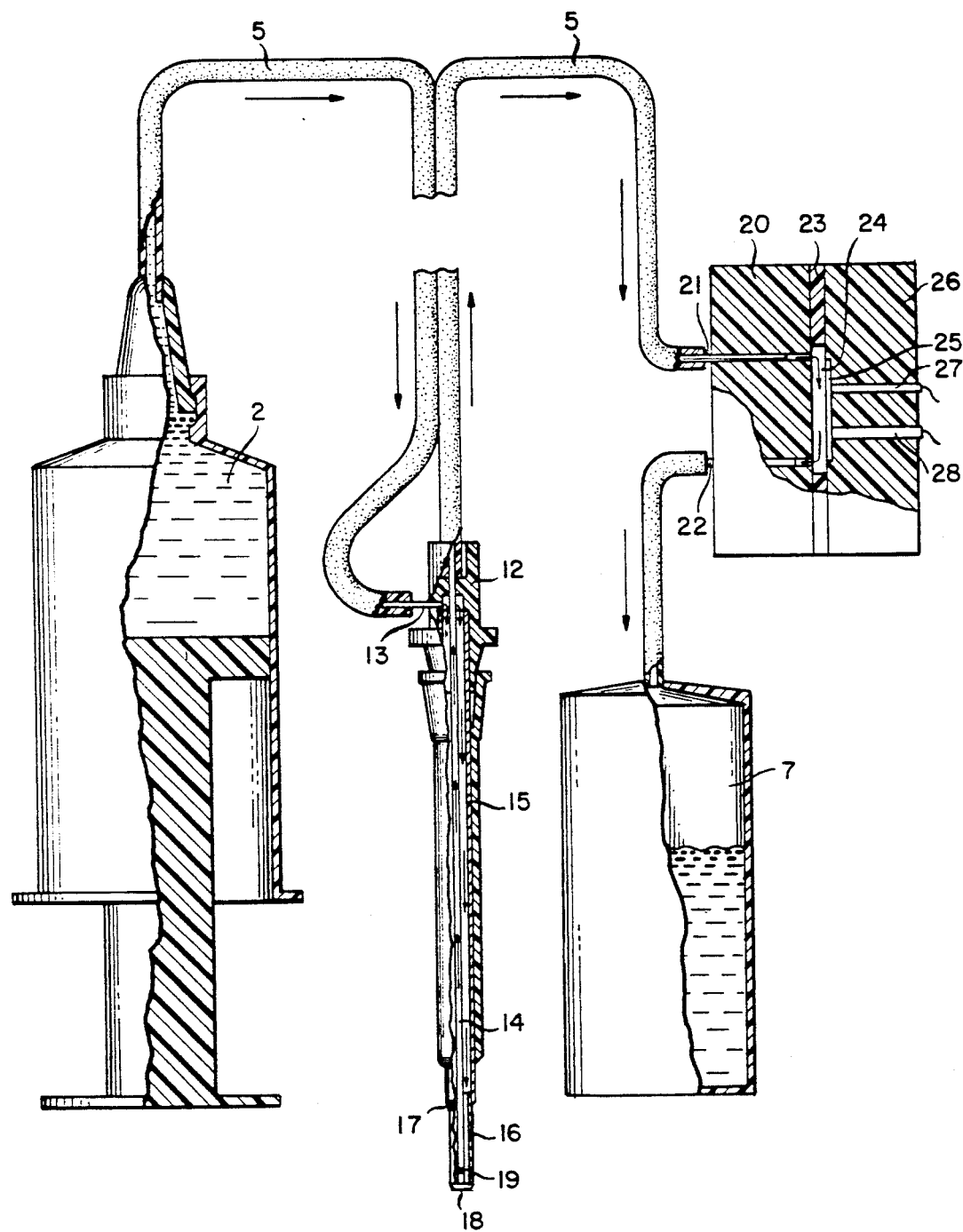
FIG. 3 is a diagram of the hydraulic system of the apparatus.
Figure 4:
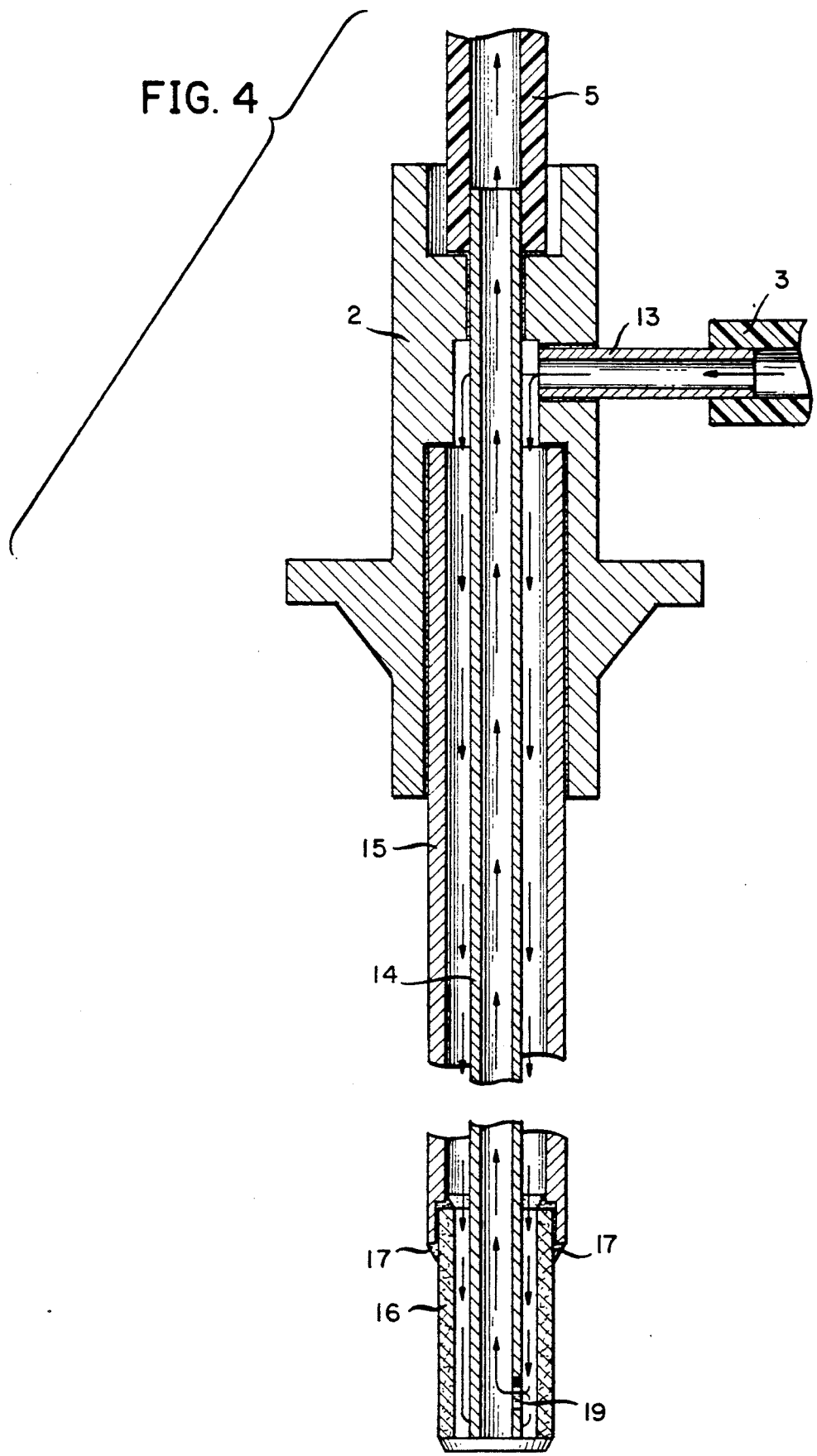
FIG. 4 is a cross section of the microdialyzing needle assembly.

The monitoring system designated by numeral 1 is the unit which continuously measures the blood glucose concentration.

By reference to the figures, numeral 2 designates a syringe which contains saline solution, in the amount of about 6 ml, with heparin. Numeral 3 is the tube of plastic material, preferably Polyvinylchloride, of internal diameter 0.1-1 mm and about 50-80 cm in length which is connected with the microdialyzing needle 4.

The physical principles of dialysis state that the concentrations of substances contained in two solutions separated by a semipermeable membrane have a tendency to become the same over a period of time because substances of low molecular weight tend to migrate from one side to the other of the membrane in order to reach equilibrium. The period of time required to reach equilibrium varies depending upon the physical properties of the semipermeable membrane and specifically the material used, the thickness, the size of the pores and upon the composition and concentration of the solutions, as well as their osmotic pressure.

One advantage of the method of the invention resides in the fact that the microdialyzing needle is inserted in the interior of a vein and may remove a portion of the low molecular weight substances present in the blood without using any means for extracorporeal circulation. During the perfusion of the needle at low flux the chemical substances enter or leave the liquid of perfusion by diffusion through the semipermeable membrane which is present on the terminal part of the needle. Thus it is possible to diffuse the heparin present in the perfusion liquid in the space surrounding the needle in order to avoid the deposit of platelets and fibrin which could affect in a short period of time the physical properties of the dialyzing membrane, and, at the same time, it is possible to remove glucose and/or other metabolites being analyzed.

Again, by varying the flux of the perfusion solution, it is possible to change the ratio of the glucose diffused from the blood in order to obtain a proportional equilibrium. Since the flux of the perfusion solution is pumped by means of a pump, it is obvious that varying the pump speed, the flux will change accordingly, and the proportional equilibrium will vary consequently.

It is therefore possible to measure a glucose concentration which is only ½-1/20 the glycemic level.

It has also been found that it is not necessary to use a syringe pump but a peristaltic pump may also be used.

In order to obtain a ratio of 1/10 between the glucose containing saline solution and the actual glucose concentration in the blood, the actual flux is 4.3 microliters/minute. For a range of ½–1/20 ratio between the glucose containing saline solution and the actual glucose concentration in the blood, the flux range is 0.1–100 microliters per minute.

The assembly of the whole micro dialyzing needle is achieved by means of a plastic piece 12 to which three steel capillaries of different dimensions are fitted and glued. The microdialyzing needle is the same as in Ser. No. 527,129.

The perfusion liquid enters the needle through the steel capillary 13 of internal diameter 0.1–0.5 mm, external diameter of 0.2–1 mm and 5–15 mm. in length which is inserted in a hole placed at right angles to the axis of the microdialyzing needle.

Two steel capillaries are assembled concentrically, the internal one 14 having an external diameter of 0.30 mm an internal diameter of 0.1 mm and a length of 79–85 mm., the external one 15 having external diameter of 0.72 mm., internal diameter of 0.40 mm. and a length of 61.5 mm. The internal diameter of the free end of the external capillary 15 is bored to a diameter of 0.50 mm. for a length of 1.5 mm.

A piece of Celanese Celgard X-20 400 um. hollow fiber of a length of 11.5–21.5 mm. designated by the numeral 16 is inserted for the length of 1.5 mm into the boring of the internal diameter of the external steel capillary and there glued with the epoxy resin 17. It must be said that the Celgard X-20 hollow fiber membrane is satisfactory for this use, both for its dimensions and for its characteristics, but other materials could be used. Again the dimensions of the used membrane depend on the cannula and on the steel capillaries used. Some epoxy resin designated by numeral 18 is again used to close and glue together the two free ends of the hollow fiber 16 and of the internal steel capillary 14. The perfusion liquid flows into the space comprised between the hollow fiber 16 and the internal steel capillary 14. The equilibrium between the perfusion liquid which gives up heparin to the exterior and the blood from which glucose, lactic acid, and other substances of low molecular weight below 100,000 daltons (if Celgard X-20 is used) diffuse to the interior of the needle through the membrane, takes place in this area.

The perfusion liquid then enters into the lumen of the internal steel capillary 14 through an opening designated by numeral 19 which serves to place into connection the external space and the internal space of the capillary at a distance of 0.5–5 mm. from the glued end.

The perfusion liquid comes out from the microdialyzing needle through the tube 5 which is set on the internal steel capillary. Specifically, this is a tube of plastic material of about 50–80 cm. in length which carries the exiting liquid from the microdialyzing needle to the measurement cell. The internal diameter of this tube is extremely small, about 0.1–1 mm., for the purpose of reducing to a minimum the period of time required for the perfusion liquid to reach the sensor thus cutting down as much as possible the latent time prior to the measurement.

The glucose sensor 6 consists of a measuring flow cell coupled with an enzymatic membrane.

The measuring cell, which is a flow cell, consists of two blocks of plastic materials screwed together and separated by a thin plastic sheet. In the first block 20, there are two holes which are the input (21) and the output (22) of the liquid coming from the microdialyzing needle to and from the measurement cell.

The thin plastic sheet 23 has an ellyptic hole in the centre (24), and in the volume having for base the ellyptic hole area and for height the thickness of the sheet, the liquid coming from the microdialyzing needle flows coming in contact with the sensor. Thus is possible to obtain a very small flow chamber which is crossed very quickly by the liquid, so shorting the latent time to a minimum.

An enzymatic membrane containing glucose oxidase 25 is placed between the plastic sheet and the second plastic block 26 in which a Platinum (27) and a Silver wire (28) electrodes are threaded and glued.

The unit of the enzymatic membrane and of the platinum and silver wires constitute the glucose sensor used to measure the glucose concentration in the liquid coming from the microdialyzing needle. The sensor is an enzymatic amperometric one in which an enzymatic reaction is coupled with an amperometric electrode. As shown hereinbelow, the glucose oxidase (GOD) adherent to the membrane catalyzes the reaction:

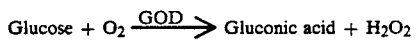

$$\text{Glucose} + O_2 \xrightarrow{\text{GOD}} \text{Gluconic acid} + H_2O_2$$

In this manner the glucose exiting from the microdialyzing needle is oxidized by the glucose oxidase contained in the membrane and is converted to gluconic acid with the production of hydrogen peroxide.

The hydrogen peroxide so produced diffuses and reaches the platinum-silver amperometric electrode. As explained above the electrode is constituted by the two silver and platinum wires threaded in the plastic block. The platinum is kept at a potential of about 650 mV with respect to the silver which serves as a reference. The potential favors the anodic dissociation of hydrogen peroxide according to the reaction:

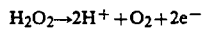

$$H_2O_2 \rightarrow 2H^+ + O_2 + 2e^-$$

In this manner two electrons are set free for each molecule of oxidized glucose, and it is therefore possible to detect an electric current in the order of tens of nanoamperes between the platinum and the silver, a current which is proportional to the concentrations of glucose in the specimen being studied.

Numeral 7 is a reservoir of plastic material which is used to collect the liquid coming out from the measuring cell.

The electronic board 29 of the system is controlled by a microprocessor, preferably made with Channel Metal Oxide Semiconductor (CMOS) technology for consumption reasons, and it is sufficient that it be an 8 bit in view of the number and the speed of the operations being performed, in this case from the family derived by Z80. The program for microprocessor functions is stored in an Erasable Programmable Read Only Memory (EPROM). By changing the program it is possible to adapt the instrument to a variety of sensors and to a variety of manners of operation. This may be necessary for concentration ranges different from the ones of blood glucose or for the conversion in different measuring units (mg < > mmol) used in foreign countries.

The microprocessor, on the basis of the program stored in the EPROM, controls the different functions carried out by the different actuators present in the monitoring unit, functions which will be described hereinbelow.

The glucose sensor 6 is polarized to about 650 mV with constant potential. A current to voltage converter simultaneously amplifies the current signal coming from the sensor to a level compatible with the input of a 10 bit analogic to digital converter which permits the microprocessor to acquire the same signal. In order to avoid that the measurements be affected by spurious disturbances which may accidentally occur, the signal is acquired and held every second by the microprocessor and the average of sixty values is calculated, and this average is considered the value of glycemia at that particular minute.

The microprocessor sends the data of the glycemia to the 8 Kbytes static CMOS Random Access Memory (RAM).

The microprocessors also commands the calibration procedures, necessary to let the sensor measures properly the glucose concentration, controlling the operations described hereinbelow. For the pourpose of calibrating the measuring system, after filling the system with the perfusion solution and prior to inserting the microdialyzing needle in the patient, the current in the absence of glucose in the specimen is measured. This current is taken as the zero or base value. During the period of time when the apparatus is connected with the patient, the operator must determine the exact glycemic level of the individual by means of an external reference. After this evaluation the operator is requested to key in the level measured by the external reference and the electric current corresponding to that value is acquired by the microprocessor. After the current revealed by the sensor on contact with the two solutions, that is, the solution at glucose zero concentration and the value determined at the known concentration are measured, the equation which represents the linear regression between two points is calculated by the microprocessor, and this regression is used as a reference to determine the concentrations present in the specimen being studied, converting the measured currents.

The microprocessor controls every second the keyboard 30 present in the device for the purpose of verifying the input of data for the initial calibration and the eventual subsequent recalibrations. The same keyboard permits in addition to command the transmission of the glycemic data after the monitoring operation period has been completed.

Another function performed by the microprocessor is the transmission of the last minute data to the alphanumeric Liquid Crystal Display 31 for the purpose of showing to the operator the value as soon as it has been measured.

The every minute transmission of last measured glycemia is necessary order to carry out the blood glucose feedback control by means of an insulin infusion system. For this purpose an Amplitude Modulation transmitter is used, the latter having a range of about 10 m. Data are being transmitted together with special codes in order to detect eventual transmission-reception errors.

At the end of the determination of the blood glucose profile, the operator may command the transmission of all every minute glycemias stored in the RAM to a personal computer so that a graphic representation of the profile can be obtained and the profile can be stored in a nonvolatile desired media.

There are also provided alarms to warn about software, measurement and hardware malfunctionings. A Light Emitting Diode and a buzzer call the attention of the operator or the patient to the fact that the instrument is not working properly.

The all monitoring system is contained in a plastic rugged box (32) which also provides a seat for the battery (33) which feeds the apparatus. Pump 8 may be a syringe pump or a peristaltic pump but other pumps could be used to provide for the advance of the perfusion solution through the apparatus. According to one embodiment the syringe pump comprises a micromotor 34 which through suitable gearings 35 causes a worm screw 36 to rotate, the latter carrying along a linear direction a small block made of plastic material 37 which in its turn pushes the piston of the syringe 2. A suitable seat facilitates the positioning of the syringe on the pump.

The infusion system 9 used in the present invention constitutes a substantial advance with respect to the infusion systems known in the art. In order to increase the flexibility of the apparatus, there is used an infusion unit programmable by a personal computer with the resolution of one minute so that the infusion profile may be obtained at a different rate from minute to minute with absolute accuracy according to the necessity of administration for different individuals. Further, the infusion system receives the data transmitted by the monitoring unit and by means of a suitable algorithm memorized in the interior of the electronic system calculates the quantity of insulin to be administered to the patient for the purpose of reaching and maintaining the predetermined desired glycemic level. This algorithm is derived by the analysis of the two caracteristic behaviours of the insulin secretion in response to the amount of glucose in the blood, the first behaviour being dependent on the actual level of glycemia, and proportional to it, and the second behaviour depending on the rate of variation, increase or decrease of the concentrations of glucose in the blood. The first behaviour is called "static control", while the second one is called "dynamic control". By using an algorithm which imitates the combination of the two behaviours, the infusion system responds very close to the actual functioning of the beta pancreatic cells and administers to the patient the proper quantity of insulin calculated every minute on the basis of the glycemic values received from the monitoring unit. The infusion profiles so calculated may be memorized in the interior of the system thus permitting the use as an insulin pump preprogrammed on the basis of the real necessity of the patient calculated with the monitoring unit without using the latter.

A syringe pump 10 similar to the one of the monitoring unit is used to push the insulin into the needle 11 inserted in the patient examined.

What is claimed:

1. A device for the continuous quantitative determination of glucose in the blood of a diabetic patient over a period of 24–36 hours, which comprises a container for a saline solution containing heparin, a microdialyzing needle inserted into a vein of said diabetic patient, pumping means for injecting said solution through said microdialyzing needle which contains a semipermeable plastic hollow fiber membrane located on its outer surface whereby dialysis occurs between the blood in the vein and said solution and only glucose and other substances of low molecular weight below 100,000 daltons go through said semipermeable fiber membrane and the concentration of said glucose and other substances of low molecular weight below 100,000 daltons reaches an equilibrium which is proportional to the actual concentration of glucose in the blood, and a glucose-containing saline solution is obtained, said microdialyzing needle being provided with an outgoing conduit, said conduit leading to a sensor, said sensor comprising a platinum silver electrode and an enzymatic membrane containing glucose oxidase, said glucose containing saline solution goes into said conduit, oxidation of glucose to gluconic acid and hydrogen peroxide occurs and said hydrogen peroxide is decomposed with the liberation of two electrons whereby electric current is produced, the concentration of glucose in the blood is determined by determining the amount of current produced, without recirculation of blood, said glucose containing saline solution contains about $\frac{1}{2}-1/20$ of the glucose concentration in the blood and said saline solution is discarded.

2. A device for the short term continuous quantitative determination of lactate in the blood of an athlete or of a heart patient, which comprises a container for a saline solution containing heparin, a microdialyzing needle inserted into a vein of said athlete or heart patient, pumping means for injecting said solution through said microdialyzing needle which contains a semipermeable plastic hollow fiber membrane located on its outer surface whereby dialysis occurs between the blood in the vein and said solution and only lactate and other substances of low molecular weight below 100,000 daltons go through said semipermeable fiber membrane and the concentration of said lactate and other substances of low molecular weight below 100,000 daltons reaches an equilibrium which is proportional to the actual concentration of lactate in the blood, and a lactate containing saline solution is obtained, said microdialyzing needle being provided with an outgoing conduit, said conduit leading to a sensor, said sensor comprising a platinum silver electrode and an enzymatic membrane containing lactate oxidase, said lactate containing saline solution goes into said conduit, oxidation of lactate to pyruvate and hydrogen peroxide occurs and said hydrogen peroxide is decomposed with the liberation of two electrons whereby electric current is produced, and the concentration of lactate in the blood is determined by determining the amount of current produced without recirculation of blood, said lactate containing saline solution contains about $\frac{1}{2}-1/20$ of the lactate concentration in the blood, and said saline solution is discarded.

* * * * *